United States Patent
Dewoolfson et al.

(10) Patent No.: US 9,399,102 B2
(45) Date of Patent: Jul. 26, 2016

(54) DEVICE AND METHOD FOR THE CONTROLLED DELIVERY OF OPHTHALMIC SOLUTIONS

(75) Inventors: Bruce H. Dewoolfson, Vienna, VA (US); Donald Harris, Newport Beach, CA (US); Mike Luttrell, Dayton, OH (US); Gabriel Carpio, San Diego, CA (US)

(73) Assignee: EUCLID SYSTEMS CORPORATION, Herndon, VA (US)

( * ) Notice: Subject to any disclaimer, the term of this patent is extended or adjusted under 35 U.S.C. 154(b) by 677 days.

(21) Appl. No.: 13/806,364

(22) PCT Filed: Jun. 24, 2011

(86) PCT No.: PCT/US2011/041795
§ 371 (c)(1),
(2), (4) Date: Feb. 8, 2013

(87) PCT Pub. No.: WO2011/163574
PCT Pub. Date: Dec. 29, 2011

(65) Prior Publication Data
US 2013/0144260 A1    Jun. 6, 2013

Related U.S. Application Data

(60) Provisional application No. 61/344,307, filed on Jun. 25, 2010.

(51) Int. Cl.
*A61M 5/42* (2006.01)
*A61F 9/00* (2006.01)
*A61K 38/17* (2006.01)
*A61K 38/45* (2006.01)
*A61M 5/32* (2006.01)

(Continued)

(52) U.S. Cl.
CPC .............. *A61M 5/427* (2013.01); *A61F 9/0017* (2013.01); *A61K 38/1709* (2013.01); *A61K 38/45* (2013.01); *A61M 5/32* (2013.01); *A61M 5/3287* (2013.01); *A61M 5/46* (2013.01); *A61K 9/0048* (2013.01)

(58) Field of Classification Search
CPC ......... A61M 5/427; A61M 5/46; A61M 5/32; A61F 9/0017
See application file for complete search history.

(56) References Cited

U.S. PATENT DOCUMENTS 6,299,603 B1 * 10/2001 Hecker ................... A61F 9/007 604/181
6,309,374 B1   10/2001 Hecker et al.
6,899,877 B2 *  5/2005 Peyman .................. A61F 2/147 128/898

(Continued)

FOREIGN PATENT DOCUMENTS

FR    2928536 A1 *  9/2009 ............ A61F 9/0017

OTHER PUBLICATIONS

International Search Report of PCT/US2011/041795, mailed Nov. 2, 2011, 2 pages.

(Continued)

*Primary Examiner* — Laura Bouchelle
(74) *Attorney, Agent, or Firm* — Lando & Anastasi, LLP

(57) ABSTRACT

The present disclosure is directed to an injector device for delivering an ophthalmic solution to a cornea of an eye. The device may include a base configured to contact part of the eye, and a needle connected to the base, wherein needle may deliver the ophthalmic solution to the cornea.

17 Claims, 11 Drawing Sheets

(51) Int. Cl.
*A61M 5/46* (2006.01)
*A61K 9/00* (2006.01)

(56) References Cited

U.S. PATENT DOCUMENTS 8,221,353 B2 * 7/2012 Cormier ............... A61F 9/0017
604/116

2010/0010452 A1 * 1/2010 Paques ................. A61F 9/0017
604/192
2011/0152749 A1 * 6/2011 Touchard ............. A61F 9/0017
604/21

OTHER PUBLICATIONS

Written Opinion of PCT/US2011/041795, mailed Nov. 2, 2011, 4 pages.

* cited by examiner

DEVICE AND METHOD FOR THE CONTROLLED DELIVERY OF OPHTHALMIC SOLUTIONS

This application claims priority to U.S. Patent Application No. 61/344,307 filed Jun. 25, 2010, the contents of which are incorporated herein by reference.

FIELD OF THE INVENTION

The present disclosure is directed to an ophthalmic solution delivery device and, more particularly, to a delivery device configured to deliver an ophthalmic solution to the stroma.

BACKGROUND

The present invention relates to devices and methods for administering ophthalmic solutions to the eye. In particular, the present invention relates to devices and methods for administering ophthalmic solutions to the portion of the cornea called the stroma. The following patents and patent applications disclose subject matter related to the present invention and the contents thereof are incorporated herein by reference in their entirety.

This application is related to:
U.S. Pat. Nos. 6,537,545, 6,946,440 and 7,402,562;
U.S. Patent Application Publication No. 2009/0105127;
U.S. Provisional Patent Application Nos. 61/241,607, filed Sep. 11, 2009, 61/266,705, filed Dec. 4, 2009, and 61/308,589, filed Feb. 26, 2010;
PCT International Publication Nos. WO 2009/114513, WO 2009/120549, WO 2009/120550; and
PCT Application No. PCT/US2007/008049, filed Apr. 3, 2007, and PCT Application No. PCT/US2010/25036, filed Feb. 23, 2010.

The cornea is the first and most powerful refracting surface of the optical system of the eye. The human cornea is a highly specialized tissue combining optical transparency with mechanical strength. It is made up of five layers, the outermost of which is the epithelium. The epithelium is only four to five cells thick, and renews itself continuously. Underneath the epithelium, the second layer is the acellular Bowman's membrane. It is composed of collagen fibrils and normally transparent. Below Bowman's membrane, the third layer, and largest part of the cornea, is the stroma. The stroma makes up approximately 90% of the cornea's thickness, and is about 500 microns (μm) thick.

The stroma comprises a well organized matrix architecture composed of approximately 200 parallel sheets of narrow-diameter collagen fibrils arranged orthogonal to neighboring fibril sheets. Corneal fibrils are primarily composed of Type I collagen co-assembled with Type V collagen. Small leucine-rich repeat proteoglycans (SLRPs), such as decorin, are critical for maintaining corneal transparency and corneal strength. The stroma is mostly water (78%) and collagen (16%), although other proteoglycans and glycoproteins are also present.

When the cornea is misshapen or injured, vision impairment can result. In the case of a misshapen cornea, eyeglasses and contact lenses have traditionally been used to correct refractive errors, but refractive surgical techniques are now also routinely used. There are currently several different techniques in use.

One such vision correction technique is radial keratotomy (RK). In radial keratotomy (RK), several deep incisions are made in a radial pattern around the cornea, so that the central portion of the cornea flattens. Although this can correct the patient's vision, it also weakens the cornea, which may continue to change shape following the surgery.

Photorefractive keratectomy (PRK) is another vision correction technique. It uses an excimer laser to sculpt the surface of the cornea. In this procedure, the epithelial basement membrane is removed, and Bowman's membrane and the anterior stroma are photoablated. However, some patients with initially good results may experience, in the months following the procedure, a change in their refraction caused by distortion of the cornea and/or other anomalies. Collectively, these changes in refraction may be referred to as "regression." In addition, corneal haze can also occur following PRK, and the greater the correction attempted, the greater the incidence and severity of the haze.

Laser in situ keratomileusis (LASIK) is yet another alternative. In this technique, an epithelial-stromal flap is cut with a microkeratome (or a laser). The flap is flipped back on its hinge, and the underlying stroma is ablated with a laser. The flap is then reseated. There is a risk that the flap created will later dislodge, however. In addition, the CRS-USA LASIK Study noted that overall, 5.8% of LASIK patients experienced complications at the three-month follow up period that did not occur during the procedure itself. These complications included corneal edema (0.6%), corneal scarring (0.1%), persistent epithelial defect (0.5%), significant glare (0.2%), persistent discomfort or pain (0.5%), interface epithelium (0.6%), cap thinning (0.1%) and interface debris (3.2%).

Most patients will have stable results after LASIK. That is, the one month to three month results will usually be permanent for most patients. However, some patients with initially good results may experience a change in their refraction (i.e., regression) over the first 3 to 6 months (and possibly longer). LASIK can result in haze as well, although less frequently than with PRK, presumably because LASIK preserves the central corneal epithelium.

The chance of having regression following LASIK is related to the initial amount of refractive error. Patients with higher degrees of myopia (−8.00 to −14.00) are more likely to experience regression. For example, a −10.00 myope may initially be 20/20 after LASIK at the 2 week follow-up visit. However, over the course of the next 3 months, the refractive error may shift (regress) from −0.25 to −1.50 (or even more). This could reduce the patient's visual acuity without glasses to less than 20/40, a point at which the patient would consider having an enhancement.

All surgical procedures involve varying degrees of traumatic injury to the eye and a subsequent wound healing process. Netto et al., Cornea, Vol. 24, pp. 509-22 (2005). Regression occurs often as a result of a reduction of biomechanical structural integrity caused by the procedure. For example, one type of postoperative regression is keratectasia. Keratectasia is an abnormal bulging of the cornea. In keratectasia, the posterior stroma thins, possibly due to interruption of the crosslinks of collagen fibers and/or altered proteoglycans composition, reducing the stiffness of the cornea and permitting it to shift forward. Dupps, W. J., J. Refract. Surg., Vol. 21, pp. 186-90 (2005). The forward shift in the cornea causes a regression in the refractive correction obtained by the surgical procedure.

In the past several years there has been increasing concern regarding the occurrence of keratectasia following LASIK. In LASIK, the cornea is structurally weakened by the laser ablation of the central stroma and by creation of the flap. While the exact mechanism of this phenomenon is not completely known, keratectasia can have profound negative effects on the refractive properties of the cornea. In some cases, the cornea thins and the resultant irregular astigmatism cannot be corrected, potentially requiring PRK to restore vision. The incidence of keratectasia following LASIK is estimated to be 0.66% (660 per 100,000 eyes) in eyes having greater than −8 diopters of myopia preoperatively. Pallikaris et al., J. Cataract Refract. Surg., Vol. 27, pp. 1796-1802 (2001). Although at present keratectasia is a rare complication of refractive surgery, the number of refractive surgical procedures performed each year continues to increase and, therefore, even this rare condition will impact many individuals. T. Seiler, J. Cataract Refract. Surg., Vol. 25, pp. 1307-08 (1999).

In addition to corneal weakening resulting from surgical procedures, other conditions involve reduced structural integrity of the cornea. For example, keratoconus is a condition in which the rigidity of the cornea is decreased. Its frequency is estimated at 4-230 per 100,000. Clinically, one of the earliest signs of keratoconus is an increase in the corneal curvature, which presents as irregular astigmatism. The increase in curvature is thought to be due to stretching of the stromal layers. In advanced stages of keratoconus, a visible cone-shaped protrusion forms which is measurably thinner than surrounding areas of the cornea.

Keratoconus may involve a general weakening of the strength of the cornea, which eventually results in lesions in those areas of the cornea that are inherently less able to withstand the shear forces present within the cornea. Smolek et al., Invest. Ophthalmol. Vis. Sci. Vol. 38, pp. 1289-90 (1997). Andreassen et al., Exp. Eye Res., Vol. 31, pp. 435-41 (1980), compared the biomechanical properties of keratoconus and normal corneas and found a 50% decrease in the stress necessary for a defined strain in the keratoconus corneas.

The alterations in the strength of the cornea in keratoconus appear to involve both the collagen fibrils and their surrounding proteoglycans. For example, Daxer et al., Invest. Ophthalmol. & Vis. Sci., Vol. 38, pp. 121-29 (1997), observed that in normal cornea, the collagen fibrils were oriented along horizontal and vertical directions that correspond to the insertion points of the four musculi recti oculi. In keratoconus corneas, however, that orientation of collagen fibrils was lost within the diseased areas. In addition, Fullwood et al., Biochem. Soc. Transactions, Vol. 18, pp. 961-62 (1990), found that there is an abnormal arrangement of proteoglycans in the keratoconus cornea, leading them to suggest that the stresses within the stroma may cause slipping between adjacent collagen fibrils. The slippage may be associated with loss of cohesive forces and mechanical failure in affected regions. This may be related to abnormal insertion into Bowman's structure or to abnormalities in interactions between collagen fibrils and a number of stabilizing molecules such as Type VI collagen or decorin. Many of the clinical features of keratoconus can be explained by loss of biomechanical properties potentially resulting from interlamellar and interfibrillar slippage of collagen within the stroma and increased proteolytic degradation of collagen fibrils, or entire lamellae.

Because both keratoconus and postoperative keratectasia involve reduced corneal rigidity, relief from each condition could be provided by methods of increasing the rigidity of the cornea. For example, methods that increase the rigidity of the cornea can be used to treat postoperative keratectasia. The treatment can be administered to a patient who plans to undergo a refractive surgical procedure as a prophylactic therapy. In other cases, the treatment can be administered during the surgical procedure itself. In still other situations, the treatment may not be initiated until after the refractive surgical procedure. Of course, various combinations of treatment before, during, and after the surgery are also possible.

It has also been suggested that a therapeutic increase in the stiffness of the cornea could delay or compensate for the softening of the cornea that occurs in keratoconus. Spoerl et al., Exp. Eye Res., Vol. 66, pp. 97-103 (1998). While acknowledging that the basis for the differences in elasticity between normal and keratoconus corneas is unknown, those authors suggest that a reduction in collagen crosslinks and a reduction in the molecular bonds between neighboring stromal proteoglycans could play a role.

There are several treatments for increasing corneal rigidity and compensating for corneal softness. Some of these treatments suffer from drawbacks that include development of corneal haze and scarring, as well as the risk of endothelial cell damage. While some of these drawbacks are associated with the particular agents used, some of these drawbacks are associated with the techniques used to administer the agents. In addition, other such treatments, while practiced with some degree of success, could benefit from enhanced delivery of the agents to the cornea. The need exists, therefore, for system that provides improved delivery of agents to the cornea.

Riboflavin has been shown to reduce the progression of keratectasia in patients with keratoconus. Aldehydes have also been used to crosslink collagen fibers and, thereby improve the structural integrity of the cornea. For example, U.S. Pat. No. 6,537,545 describes the application of various aldehydes to a cornea in combination with a reshaping contact lens. The contact lens is used to induce the desired shape following either enzyme orthokeratology or refractive surgery, and the aldehyde is used to crosslink collagens and proteoglycans in the cornea. However, application of such agents can be problematic.

In addition, small leucine-rich repeat proteoglycans (SLRPs), such as decorin; fibril-associated collagens with interrupted triple helices (FACITs); or the enzyme transglutaminase, can be used to retard relaxation of corneal tissue back to the original curvature when used as an adjunct to an orthokerotological procedure. See U.S. Pat. No. 6,946,440. However, while there have been devices developed to contain solutions in an area on the surface of the cornea (see e.g., PCT International Publication No. WO 2009/120550), there has not been a delivery device that facilitates introduction of such agents directly into the subsurface portions of the stroma.

Although orthokeratology and surgical techniques such as LASIK seek to improve visual acuity using radically different approaches, the success of both orthokeratology and surgical techniques may be improved by increasing structural integrity of the cornea. Despite the fact that surgery disrupts the cornea and removes corneal tissue, methods of stabilizing collagen fibrils using proteins that crosslink the collagen fibrils, such as decorin or the enzyme transglutaminase, have been shown to improve the outcome following a surgical procedure to improve visual acuity. Those results also provide a basis for treating diseases of the cornea, such as keratectasia from other causes, such as keratoconus.

In addition to agents that increase the structural integrity of the cornea, there may be a desire to deliver other types of ophthalmic solutions, such as antibiotics and/or other agents, to the cornea.

For a number of different ophthalmic agents, it may be advantageous to deliver such agents directly to subsurface portions of the stroma. Although certain agents may be applied topically, in order to achieve penetration to a desired depth within the cornea, it is sometimes necessary to pretreat the cornea with agents that enhance penetration, such as agents that dissociate epithelial cell junctures. Further, even with penetration-enhancing agents, satisfactory penetration of agents to the desired depth of the cornea may not always be achievable.

The present disclosure is directed to improvements in delivery of ophthalmic solutions to the cornea.

BRIEF SUMMARY

The present disclosure is directed to an injector device configured to deliver an ophthalmic solution to a cornea of an eye, wherein the device may include a base and a needle. The base of the device may be configured to contact a portion of the eye, and the needle may be connected to the base and configured to deliver the ophthalmic solution to the cornea.

The present disclosure is also directed to an injector device configured to deliver an ophthalmic solution to a cornea of an eye, wherein the device may include a base including at least one locator member, a needle, and a needle holding member. The at least one locator member may be configured to contact a portion of the eye. The needle may be connected to the base and configured to be inserted into the cornea to deliver the ophthalmic solution to the cornea. The needle-holding member may be connected to the base, and the needle may be disposed within the needle-holding member. The needle-holding member may also be configured to translate the needle relative to the base to insert the needle into the cornea.

The present disclosure is further directed to the method of delivering of an ophthalmic solution to a cornea of an eye. Delivery of the solution may be accomplished by positioning an injector device so that a base of the device contacts a portion of the eye. A needle, which is connected to the base, may then be inserted into the cornea, and the ophthalmic solution may be delivered to the cornea through an interior of the needle.

It is to be understood that both the foregoing general description and the following detailed description are exemplary and explanatory only and are not restrictive of the invention.

DETAILED DESCRIPTION OF THE INVENTION

Figure 1:
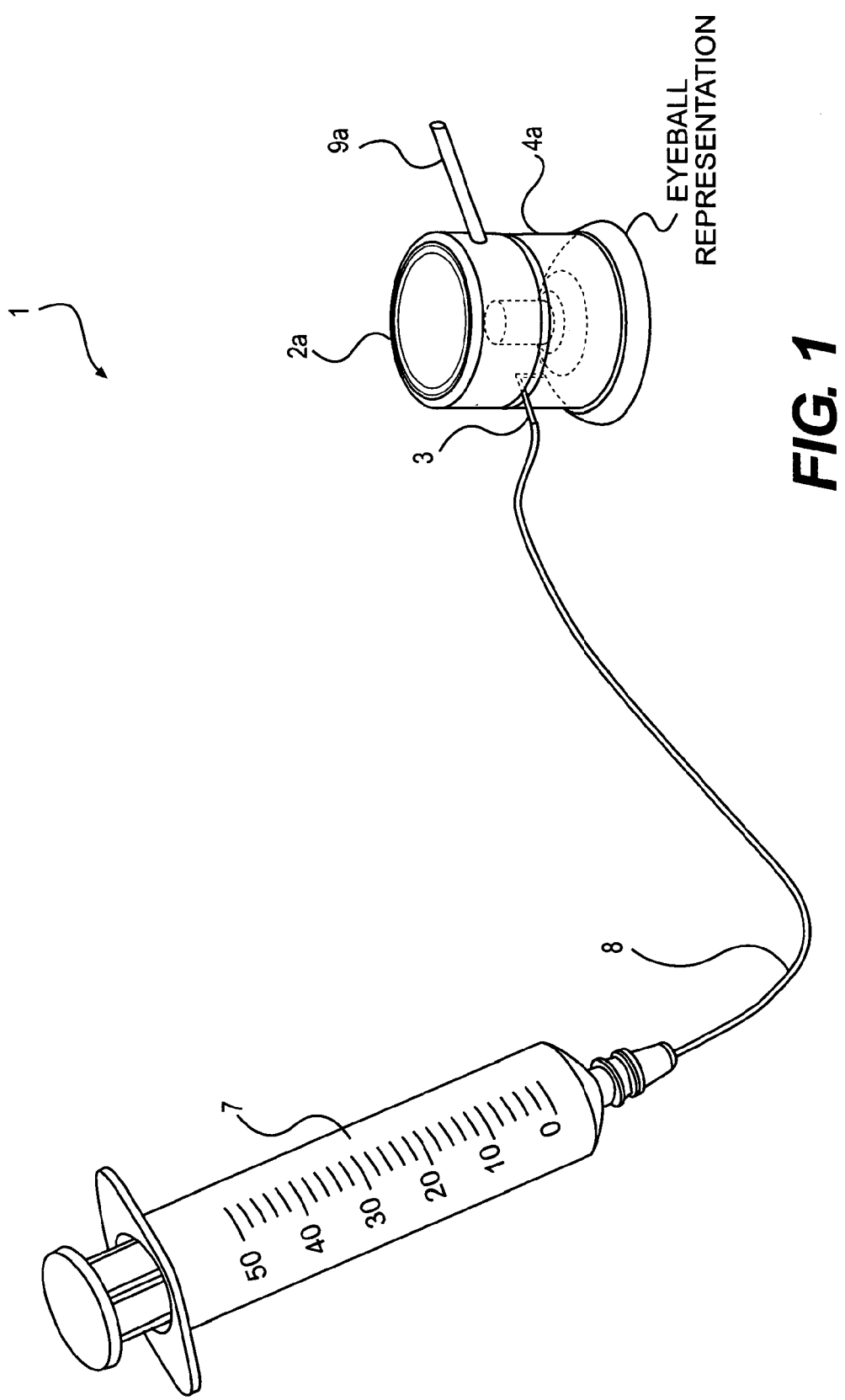
FIG. 1 illustrates an exemplary embodiment of the disclosed injector device.

In order that the present invention may be more readily understood, certain terms are first defined. Other definitions are set forth throughout the description of the embodiments.

I. Definitions

A "refractive surgical procedure" includes, but is not limited to, Radial Keratotomy (RK), Photorefractive Keratoplasty (PRK), LASIK (Laser-Assisted In Situ Keratomileusis), Epi-LASIK, IntraLASIK, Laser Thermal Keratoplasty (LTK), and Conductive Keratoplasty.

"Stabilizing" includes increasing the rigidity, as measured by the Corneal Response Analyzer manufactured by Reichert Ophthalmic Institute. This instrument gives a quantitative measure of corneal rigidity called the Corneal Resistance Factor (CFR) and also a quantitative measure of corneal historesis (CH). "Stabilizing" can also mean decreasing the ability of one collagen fibril to move relative to another collagen fibril by virtue of increased intermolecular interactions.

"Crosslinks" includes the formation of both direct and indirect bonds between two or more collagen fibrils. Direct bonds include covalent bond formation between an amino acid in one collagen fibril and an amino acid in another fibril. For example, the transglutaminase family of enzymes catalyze the formation of a covalent bond between a free amine group (e.g., on a lysine) and the gamma-carboxamide group of glutamine. Transglutaminase thus is not itself part of the bond. Indirect bonds include those in which one or more proteins serve as an intermediary link between or among the collagen fibrils. For example, decorin is a horse-shoe shaped proteoglycan that binds to collagen fibrils in human cornea forming a bidentate ligand attached to two neighboring collagen molecules in the fibril or in adjacent fibrils, helping to stabilize fibrils and orient fibrillogenesis. Scott, J E, Biochemistry, Vol. 35, pages 8795 (1996).

A "protein that crosslinks collagen fibrils" includes proteins that form direct or indirect crosslinks between two or more collagen fibrils. Examples include decorin and transglutaminase. In certain embodiments, a protein that crosslinks collagen fibers is not a hydroxylase, such as lysyl oxidase or prolyl oxidase.

"Transglutaminase" includes any of the individual transferase enzymes having the enzyme commission (EC) number EC 2.3.2.13. Examples of human transglutaminase proteins include those identified by the following REFSEQ numbers: NP_000350; NP_004604; NP_003236; NP_003232; NP_004236; NP_945345; and NP_443187. Besides human transglutaminase, transglutaminase prepared from non-human sources is included within the practice of the invention. Examples of non-human sources include, but are not limited to, primates, cows, pigs, sheep, guinea pigs, mice, and rats. Thus, in one embodiment, the transglutaminase is a transglutaminase solution prepared from an animal source (e.g., Sigma Catalogue No. T-5398, guinea pig liver). In other embodiments, however, the transglutaminase is from a recombinant source, and can be, for example, a human transglutaminase (e.g., the transglutaminase available from Axxora, 6181 Cornerstone Court East, Suite 103, San Diego, Calif. 92121 or from Research Diagnostics, Inc., a Division of Fitzgerald Industries Intl, 34 Junction Square Drive, Concord Mass. 01742-3049 USA).

"Decorin" includes any of the proteins known to the skilled artisan by that name, so long as the decorin functions as a bidentate ligand attached to two neighboring collagen molecules in a fibril or in adjacent fibrils. Thus, "decorin" includes the core decorin protein. In particular, decorin proteins include those proteins encoded by any of the various alternatively spliced transcripts of the human decorin gene described by REFSEQ number NM_001920.3. In general, the human decorin protein is 359 amino acids in size, and its amino acid sequence is set forth in REFSEQ number NP_001911. Various mutations and their effect on the interaction of decorin with collagen have been described, for example by Nareyeck et al., Eur. J. Biochem., Vol. 271, pages 3389-98 (2004), and those mutants that bind collagen are also within the scope of the term "decorin," as is the decorin variant known as the 179 allelic variant (see De Cosmo et al., Nephron, Vol. 92, pages 72-76 (2002)). Decorin, for use in the disclosed methods, may be from various animal sources, and it may be produced recombinantly or by purification from tissue. Thus, not only human decorin, but decorin from other species, including, but not limited to, primates, cows, pigs, sheep, guinea pigs, mice, and rats, may also be used in the disclosed methods. An example of human decorin that can be used in the disclosed methods is the recombinant human decorin that is available commercially from Gala Biotech (now Catalant). Glycosylated or unglycosylated forms of decorin can be used.

As used herein, the terms "treatment," "treating," and the like, refer to efforts to obtain a desired pharmacologic and/or physiologic effect. A treatment can administer a composition or product to a patient already known to have a condition. A treatment can also administer a composition or product to a patient as part of a prophylactic strategy to inhibit the development of a disease or condition known to be associated with a primary treatment. In the context of a surgical procedure, prophylactic treatment is any treatment administered to a patient scheduled to undergo a surgical procedure for the purpose of improving the outcome of that surgical procedure or otherwise reducing undesirable secondary effects associated with the surgical procedure. An example of a prophylactic treatment is the administration of an immunosuppressive agent to a patient prior to the transplantation of an organ or tissue. "Treatment," as used herein, covers any treatment of a condition or disease in a mammal, particularly in a human, and includes: (a) inhibiting the condition or disease, such as, arresting its development; and (b) relieving, alleviating or ameliorating the condition or disease, such as, for example, causing regression of the condition or disease.

The terms "individual," "subject," "host," and "patient," used interchangeably herein, refer to a mammal, including, but not limited to, murines, simians, humans, felines, canines, equines, bovines, porcines, ovines, caprines, mammalian farm animals, mammalian sport animals, and mammalian pets.

II. Injector Device

The present disclosure is directed to a device 1 for delivering an ophthalmic solution to a cornea of an eye. The device 1 may include a base, a needle-holding member, and a needle, wherein the device 1 is configured to regulate insertion of the needle to a depth within the stroma.

The base 2a, 2b may include at least one eye-contacting locator member 4a, 4b. The locator member 4a, 4b may be configured to contact portions of the eye surrounding the central region of the cornea. For example, the locator member 4a, 4b may be configured to contact the cornea in such a way as to facilitate insertion of the needle 3 into the limbus (i.e., for LASIK patients, the limbus is approximately between the edge of the flap and the visual path of the eye). As shown in FIG. 1, the locator member 4a may be a flexible cylindrical element that flexes a predetermined amount in order to allow penetration of the needle 3, which may be fixedly attached to an upper, more rigid part of the base 2a that serves as the needle-holding member. In some embodiments, the locator member 4a may include a bellows.

The needle 3 may be a microneedle, having a gauge and length suitable for delivering ophthalmic solutions to the stroma. The epithelium is approximately 50 μm thick, and the stroma is approximately 350-450 μm thick. Therefore, in some embodiments, the needle 3 may have a length that enables penetration of the needle 3 approximately 50-450 micrometers (μm) into the corneal tissue. In some embodiments, the injector device 1 may be configured to regulate insertion of the needle 3 to a depth of about 250 μm (roughly halfway) into the stroma. Following laser surgeries, the stromal bed is exposed, either via laser ablation of the epithelium or microkeratome slicing of the epithelial flap. Therefore, in some embodiments, needle penetration of less than 50 μm may be desirable and is, therefore, envisaged. One exemplary gauge of needle is a 32 gauge needle, although needles of a variety of gauges could be used.

The injector device 1 may include one or more needles 3. In some applications, it may be desirable to inject ophthalmic solution into more than one location of the cornea. In such cases, the injector device 1 may be configured to be positioned in more than one way (either via translation or rotation of the base 2a, 2b relative to the eye) in order to facilitate insertion of the needle 3 in multiple locations. The base 2a, 2b may rotate with, or independent of, the locator member(s) 4a, 4b. In some embodiments, the injector device 1 may include multiple needles 3 for injecting in multiple locations. In some cases multiple injections may be made simultaneously. In addition to injections at multiple locations, the injector device 1 may be configured to perform injections at multiple depths. In some embodiments, injections at multiple depths may be performed simultaneously by multiple needles 3.

Figure 3:
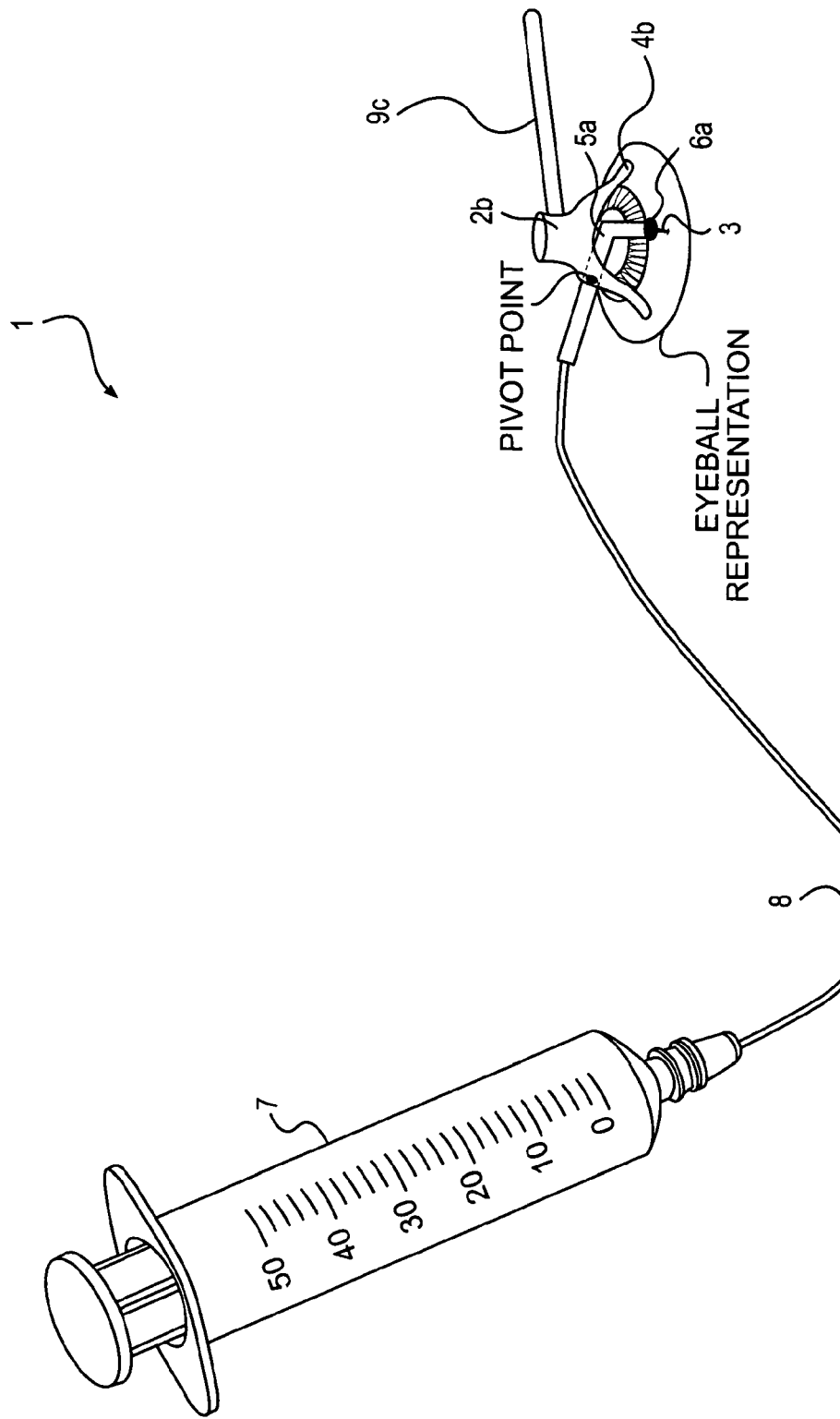
FIG. 3 illustrates an additional exemplary embodiment of the disclosed injector device.
Figure 4:
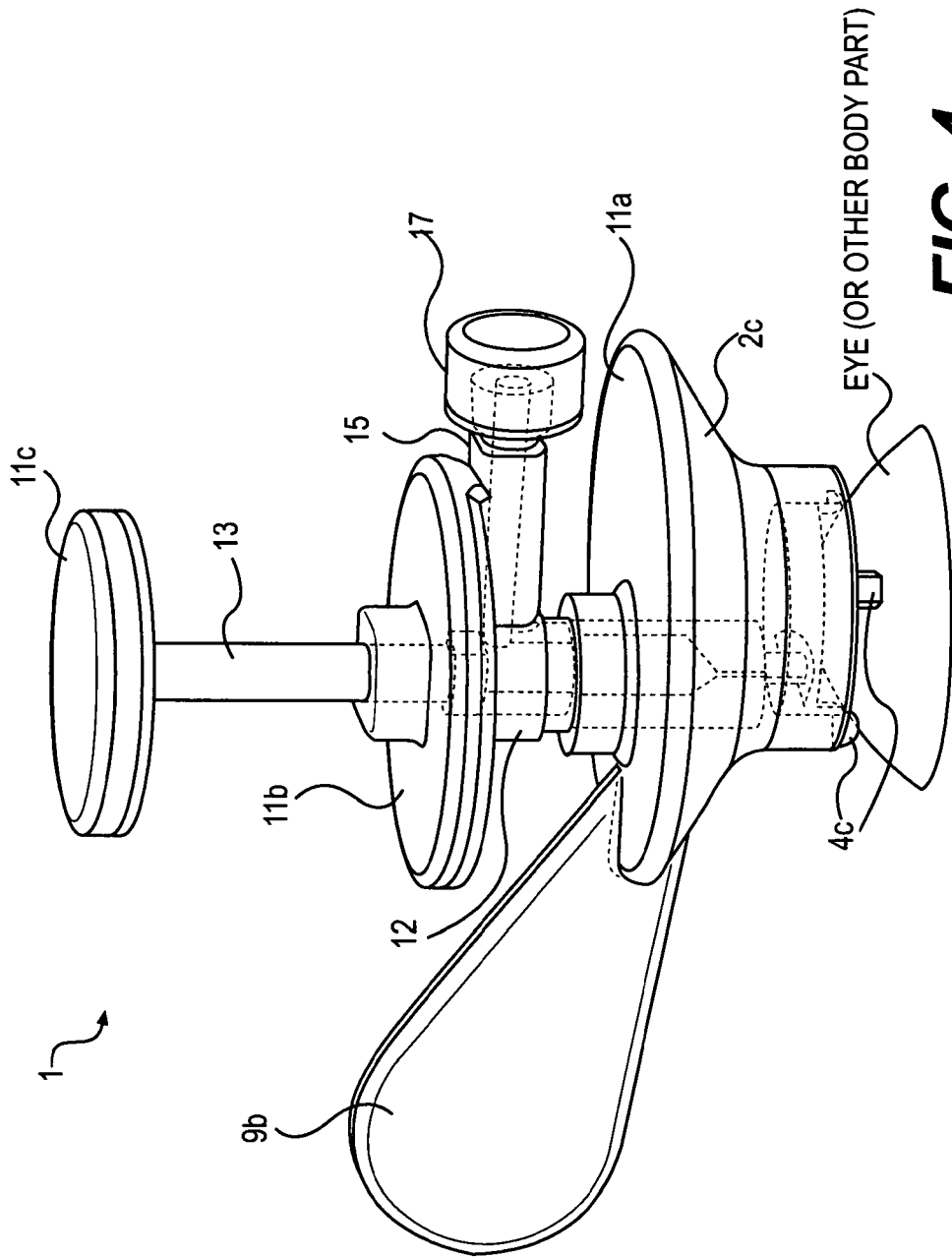
FIG. 4 illustrates a further exemplary embodiment of the disclosed injector device with interior components shown with dashed lines.

In addition, in some embodiments, the injector device 1 may include a needle penetration limiting element 6a, 6b. For example, as shown in FIG. 3, the needle may include a penetration limiting element 6a, which is a stopper, at the base of the needle 3, or along the shaft of the needle 3, to prevent penetration of the needle 3 past the stopper 6a. The stopper 6a may be in any suitable shape, e.g., a ball (as shown in FIG. 3) or a disc. In other embodiments, the structure of other injector components may limit needle penetration. For example, in the embodiment shown in FIG. 1, the amount by which the locator member 4a flexes may determine and, therefore, limit needle penetration.

The injector device 1 may also include a reservoir 7 fluidly connected to the needle 3, e.g., via tubing 8. Although the reservoir 7 is shown in the figures to be in the form of a syringe that is separate from the base 2a, 2b, various alternative reservoir embodiments are possible. For example, in some embodiments, the reservoir 7 may be a squeeze bottle, or a blow-fill sealed polyurethane bottle. Such reservoirs 7 may be separate from, or integral with, the base 2a, 2b, and may be in fluid communication with the needle 3 using any suitable means, e.g., tubing 8. In some embodiments, the base 2a, 2b may include a chamber, which may be prefilled and/or refillable with solution.

In some embodiments, the needle-holding member 5a may be in the form of an armature or the like. For example, in FIG. 3, an embodiment is shown including a needle-holding member 5a, which pivots relative to the base 2b in order to facilitate insertion of the needle 3 into the cornea. Other configurations of actuatable needle-holding members are also envisioned.

In some embodiments, the injector device 1 may include one or more rigid locator members 4a, 4b. In some embodiments, the injector device 1 may include a cylindrical locator member 4a, such as shown in FIG. 1, wherein the cylindrical locator member 4a is rigid. In such embodiments, the needle-holding member 5a may be actuatable. In other embodiments, the injector device 1 may include several locator members 4b, as shown in FIG. 3. The embodiment shown in FIG. 3 may include any suitable number of locator members 4b. For example, as shown in FIG. 3, there may be three locator members 4b in the form of a tripod (note: one of the locator members 4b extends from the back side of the base 2b, and thus, is not shown in FIG. 3).

In some embodiments, the reservoir 7 may have a configuration that is not readily recognizable as a syringe, in order to avoid patient concern related to needles. Further, the means by which delivery of the solution from the reservoir 7 into the eye is triggered may be inconspicuous. For example, the reservoir 7 may have a small thumb lever on the side of the reservoir to trigger injection of solution.

The injector device 1 may include a handle 9a, 9b, 9c for gripping the base 2a, 2b while holding the locator member 4a, 4b against the eye. The handle 9a, 9b, 9c may have any suitable shape. Although a substantially cylindrical handle 9a, 9b, 9c is shown in the accompanying figures, other shapes are envisioned, e.g., flat, corrugated, mug-handle type, etc. In some embodiments, the injector device 1 may include more than one handle attached, or attachable, to the base 2a, 2b.

Figure 2:
FIG. 2 illustrates another exemplary embodiment of the disclosed injector device.

The handle 9a, 9b, 9c may be located in a variety of places. For example, as shown in FIG. 2, the handle 9a, 9b, 9c may be located close to tubing 8 that connects to the reservoir 7. In other embodiments, the handle 9a, 9b, 9c may be located opposite the tubing 8. (See FIG. 3). In still other embodiments, the handle 9a, 9b, 9c may be located at a predetermined angle (e.g., approximately 120-170 degrees) from the tubing 8, in order to avoid contact of the handle 9a, 9b, 9c or the tubing 8 with the bridge of the patient's nose.

In some embodiments, the handle 9a, 9b, 9c may be detachable from the base 2a, 2b. For example, as shown in FIG. 2, the handle 9b may screw into the base 2a. The base 2a may include multiple holes 10 for receiving a threaded handle 9b in order to allow customization according to user preference. In addition, the injector device 1 may include and/or be configured to receive handles of different shapes, again, according to user preference.

Also, the handle shape and/or placement may be ambidextrous in some embodiments. In other embodiments, the handle shape and/or placement may be right and left specific. Right and left specificity may be with regard to administration of solutions to a right or left eye. Alternatively, or additionally, the right and left specificity may be with respect to the preference of the user to hold the injector device 1 with their left or right hand.

The methods of strengthening the cornea in association with a surgical procedure may be initiated at any of a variety of time points after the patient has been informed that surgery is needed, or informed that surgery is an option for that patient. For example, a patient considering LASIK may receive the strengthening treatment at the time of his or her LASIK prescreening examination. Alternatively, the strengthening treatment may be administered at a time between the prescreening exam and the surgery. In general, the strengthening treatment will take place within the month preceding the surgery, although, in some cases the time period may be more than a month before the surgery. For example, it is possible that the strengthening treatment could be administered 5, 6, 7, 8, or even more weeks before. Usually, however, the strengthening treatment will be administered about one to two weeks before the corneal surgery. Often, when it is administered before surgery, the strengthening treatment will be administered about 10 days before the surgery, although it may be administered about 9, about 8, about 7, about 6, about 5, about 4, about 3, about 2, or about 1 days before the corneal surgery. It is also possible to treat the cornea on the same day as the corneal surgery.

In other embodiments, the strengthening treatment takes place during the surgical procedure. These embodiments do not exclude treatments at other times, such as before and/or after the surgical procedure. Varying the amount of ophthalmic solution used when the strengthening treatment takes place during the surgical procedure is within the scope of the disclosed embodiments. The amount of solution administered will depend at least in part upon the concentration of the agent in the solution used, as well as the potency of the particular agent, and the severity of the condition being treated. The amount administered may also depend on whether multiple injections will be given, either over time, or at different locations of the cornea. The selection of the amount of solution to be administered may be left to the discretion of the practitioner during individual procedures. One exemplary dosage of agents is between 7 μL and 15 μL per injection site, although dosages less than 7 μL or more than 15 μL per injection site could be administered.

Another exemplary embodiment is illustrated in FIGS. 4-8. As shown in FIGS. 4-8, the injector device 1 may include a substantially flat handle 9d, which may be oriented substantially vertically as shown, and may be configured for gripping with two digits of the hand, (e.g., the finger and thumb). The handle 9d may have two parallel sides or may have opposing concave sides, e.g., contoured to mate with a users fingers.

As also shown in FIGS. 4-8, the injector device 1 may include one or more locator members 4c configured to position the device 1 on the surface to be pierced by the needle 3. The base 2c may include a flange 11a. The device 1 may include a two-piece plunger assembly. A first plunger piece 12 of the plunger assembly may include a needle-holding member 5b, and may translate with respect to the base 2c, toward and away from the surface to be pierced. The first plunger piece 12 may include a hollow cavity 14 in which solution to be injected may be housed. A tube, preferably made of stainless steel, can be molded into the hollow cavity 14 to form a barrel of the delivery device 1. In addition, the injector device 1 may include a second plunger piece 13 configured to be telescopically inserted within the hollow cavity 14 of the first plunger piece 12 in order to expel solution from the first plunger piece 12, or telescopically withdrawn from the hollow cavity 14 to withdraw material and/or liquid into the hollow cavity 14 through the needle 3. The first plunger piece 12 may also include an inlet/outlet port 15 through which fluids may be introduced to or removed from the hollow cavity 14.

Figure 5:
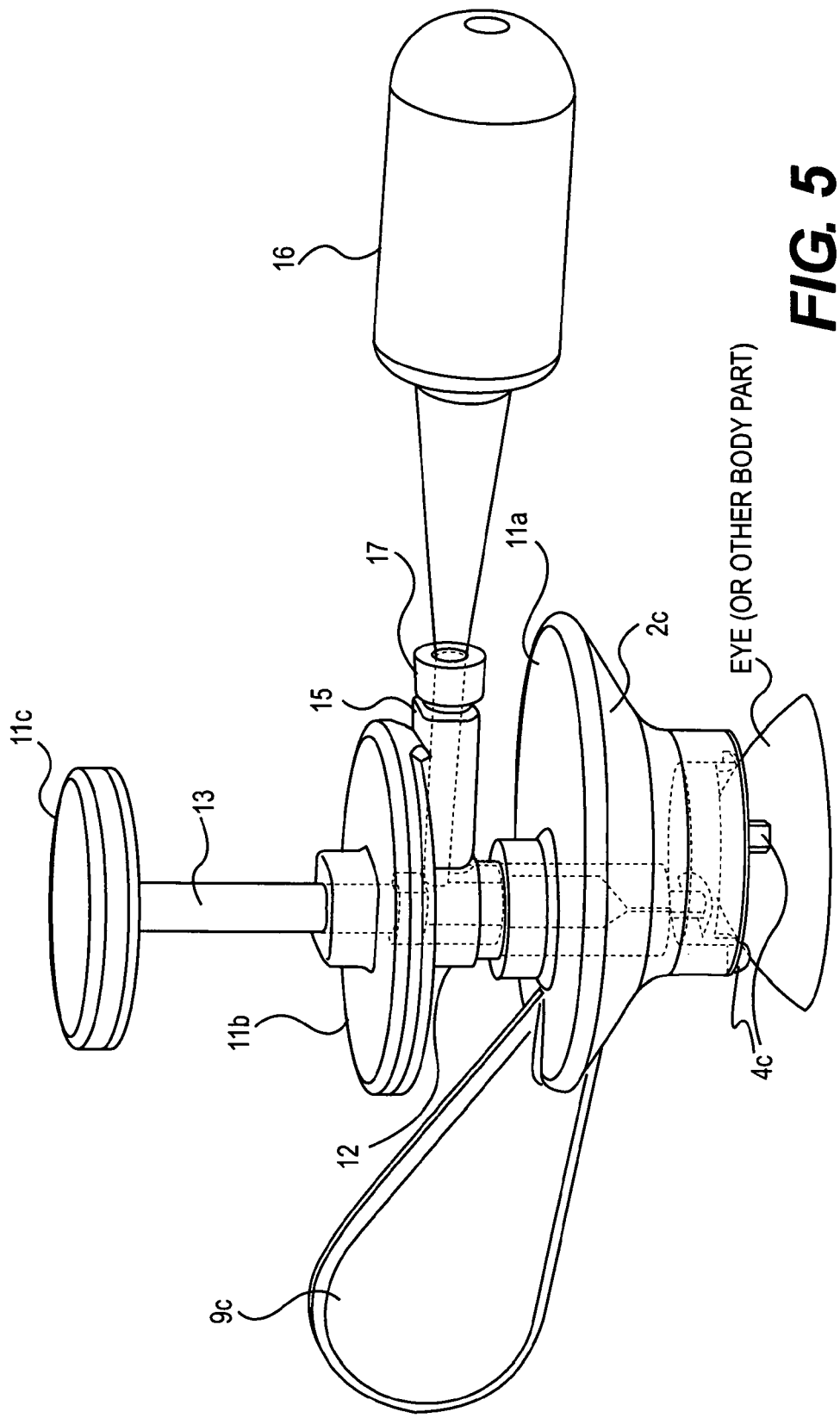
FIG. 5 illustrates the injector device of FIG. 4 with a squeeze bulb element inserted therein.
Figure 6:
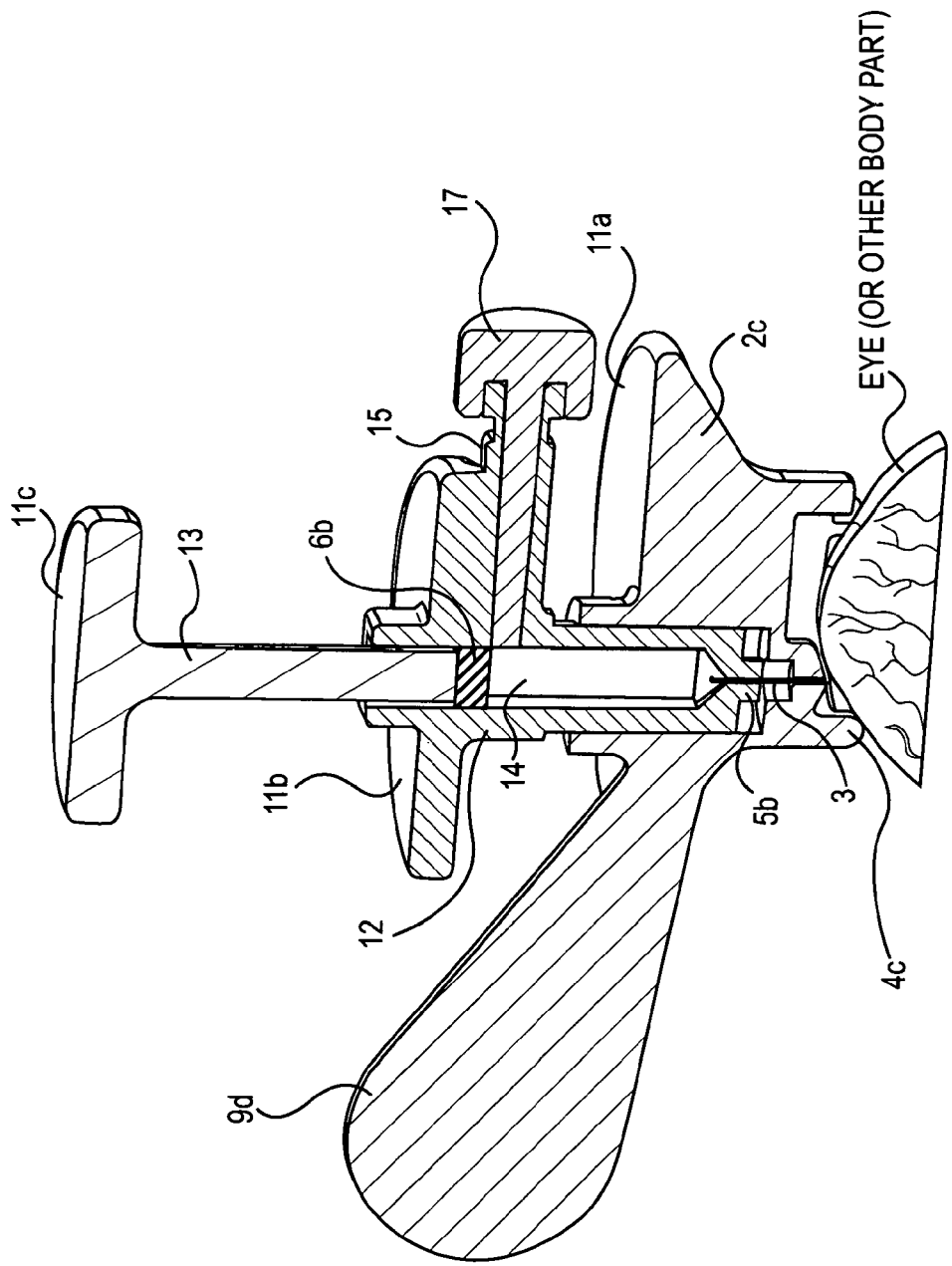
FIG. 6 illustrates a cross-sectional view of the injector device of FIG. 4 with a plunger assembly that has not been actuated.
Figure 7:
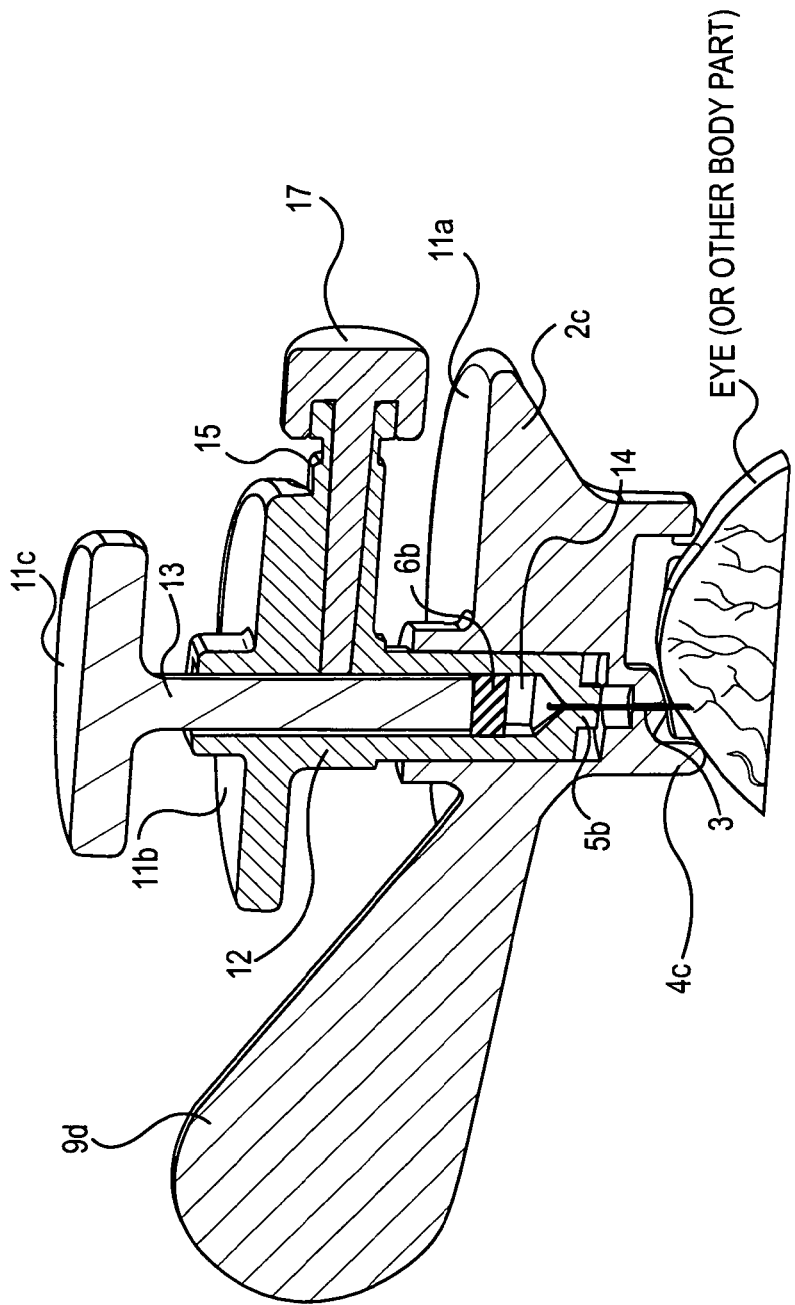
FIG. 7 illustrates a cross-sectional view of the injector device of FIG. 4 with a plunger assembly that has been actuated.
Figure 8:
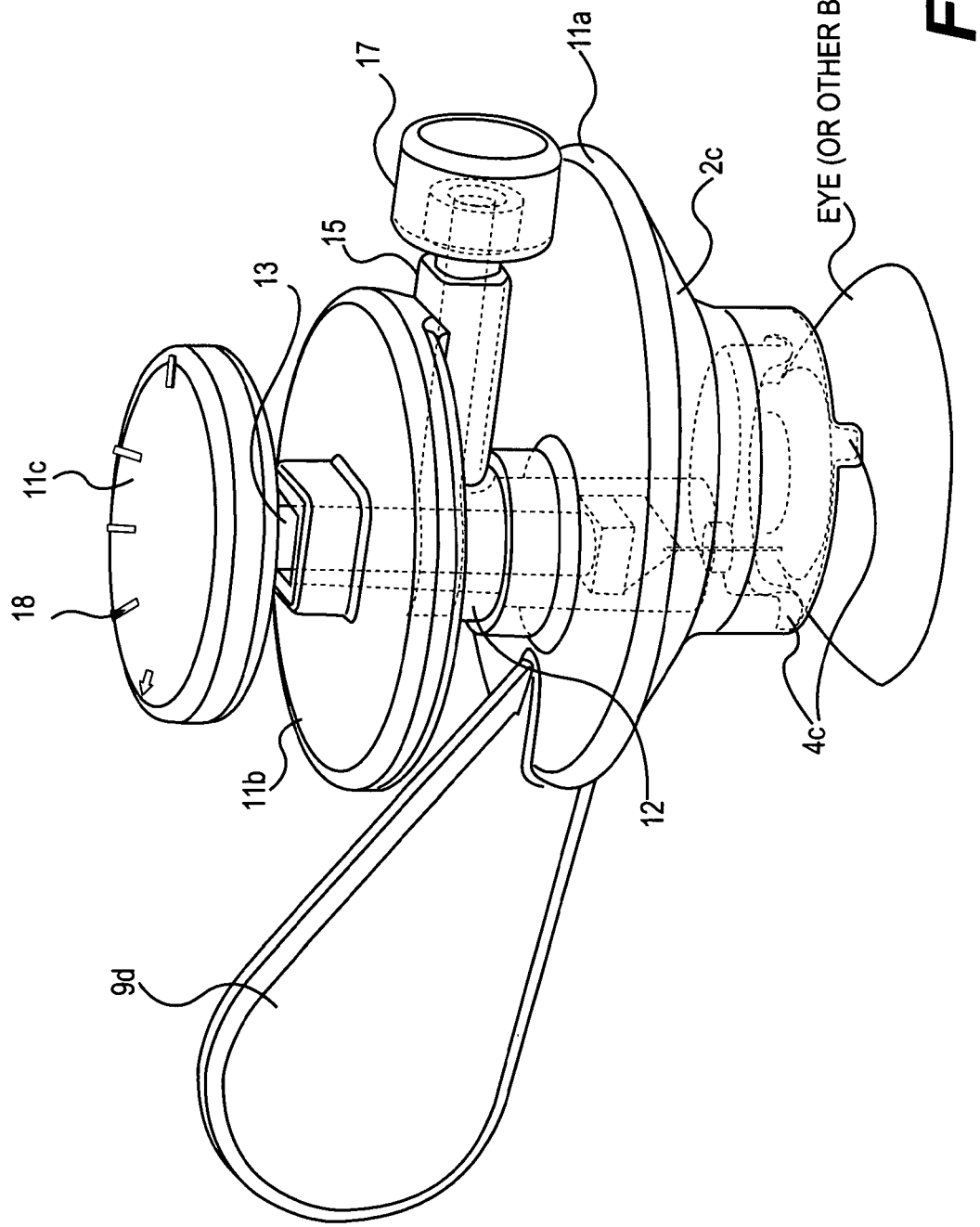
FIG. 8 is a top perspective view of the injector device shown in FIG. 4.

As shown in FIG. 5, the injector device 1 may include a removable squeeze bulb element 16 for introducing to, or removing material from, the hollow cavity 14 via the inlet/outlet port 15. In addition, the injector device 1 may include a plug 17 for the inlet/outlet port 15, as shown in FIG. 6.

Also, the injector device 1 may include flanges 11b, 11c on the first plunger piece and/or on the second plunger piece, respectively, which may, in conjunction with the flange 11a on the base 2c, facilitate actuation of the plunger pieces 12, 13 with respect to the base 2c and each other.

In addition, as shown in FIGS. 4-8, the injector device 1 may be configured to administer an injection offset from a center line of the device 1. As shown, the needle 3, first plunger piece 12, and second plunger piece 13 may be disposed off center, e.g., to avoid injection directly into the cornea in the line of sight of the patient.

Additionally, the injector device 1 may include indicator markings 18 located on the flange 11c of the second plunger piece 13. These indicator markings 18 are advantageous in that they provide a clearer indication of the flange 11c of the second plunger piece 13 being a desired position. While the flange 11c of the second plunger piece 13 is being rotated, the indicator markings 18 are capable of identifying different filling and dosing positions for administering different doses of the ophthalmic solution to a patient. When one of the indicator markings 18 is aligned with the inlet/outlet port 15, the flange 11c of the second plunger piece 13 can be advanced to provide a dosage associated with the aligned indicator marking. The indicator markings 18 can additionally comprise an arrow marking. The user can align the arrow with the inlet/outlet port 15, remove the plug 17, and subsequently fully retract the flange 11c. Thereafter the user can advance the second plunger piece 13 to purge the air, and install the plug 17 onto the inlet/outlet port 15.

During operation, after the flange 11c has been fully retracted and the plug 17 has been installed onto the inlet/outlet port 15, dosages can be provided. The practitioner can rotate the flange 11c to align one of the indicator markings 18 with the inlet/outlet port 15. Where an arrow indicator marking is used as the indicator for full retraction of the flange, the indicator marking located adjacent the arrow indicator marking may correspond to a first dose to be administered. Each indicator marking 18 may correspond to a different dose to be provided during operation of the injection device. A practitioner may administer additional doses by rotating the flange 11c and aligning indicator markings 18 with the inlet/outlet port 15 before advancing the second plunger piece 13 to deliver a corresponding dose.

The disclosed devices and methods have been described generally. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

INDUSTRIAL APPLICABILITY

The disclosed injector device may be applicable for administering an ophthalmic solution to the eye of a patient. In particular, the injector device may be configured to deliver ophthalmic solutions to the front (i.e. anterior) of the eye.

The disclosed injector device can be used to inject ophthalmic solutions to a subsurface region of the stroma. Exemplary uses for such injections may include treatments for, and/or prevention of, "front-of-the-eye" conditions, such as myopia, hyperopia, astigmatism, keratectasia, and keratoconus, by administering agents that improve the structural integrity of the cornea, e.g., by increasing its rigidity. Such uses may include stabilizing the cornea, correcting refractive error, and improving unaided visual acuity. For example, exemplary treatments may be administered in conjunction with refractive surgery procedures, such as LASIK, PRK, RK, and other surgical refractive procedures. In addition, exemplary treatments may include, or may be associated with, non-surgical refractive procedures, such as orthokeratology and corneal rehabilitation.

In addition, the disclosed device may be utilized to administer agents to the cornea for the purpose of rendering the cornea more malleable and/or pliable (e.g., corneal acylation). This procedure may be performed prior to a stabilization procedure not associated with a surgical treatment.

Possible agents shown to increase structural rigidity of the cornea include compositions with proteins that crosslink collagen fibrils. Exemplary compositions may include such proteins along with a pharmaceutically acceptable carrier. For example, decorin crosslinks the collagen fibrils by binding to each of two different fibrils to form a bridge therebetween. Another such protein is transglutaminase, which crosslinks collagen fibrils by catalyzing the formation of a covalent bond between an amino acid in one collagen fibril and an amino acid in a second collagen fibril. The disclosed injector device may be utilized to inject compositions including decorin or transglutaminase.

In one exemplary embodiment, such agents may be administered by the disclosed injector device to the cornea subject to a refractive surgical procedure. The treatment may be initiated before, during, and/or after the surgery. Exemplary refractive surgical procedures may include, but are not limited to, Radial Keratotomy (RK), Photorefractive Keratoplasty (PRK), LASIK (Laser-Assisted In Situ Keratomileusis), Epi-LASIK, IntraLASIK, Laser Thermal Keratoplasty (LTK), and Conductive Keratoplasty.

The disclosed injector device may be employed in methods of treating keratectasia, comprising administering to the stroma a composition comprising a protein that crosslinks collagen fibrils and a pharmaceutically acceptable carrier. The treatment can be prophylactic, contemporaneous with a surgical procedure, postoperative, or can involve multiple administrations during one or more of those time points. Although the keratectasia may develop following a refractive surgical procedure, such as LASIK, it may also develop in an eye that has not had a surgical procedure.

The disclosed injector device may be employed in methods of treating keratoconus, comprising administering to the eye of a patient who has keratoconus a composition comprising a protein that crosslinks collagen fibrils and a pharmaceutically acceptable carrier.

EXAMPLE

Comparison of Corneal Hysteresis in LASIK Patients Superficial Decorin Eye Drops vs. Needle-Injected Decorin Testing has shown that needle injection of decorin to subsurface regions of the stroma produce greater improvements than merely administering drops containing decorin to the stromal bed. The following data illustrates the benefit of subsurface injections as compared to superficial drops.

Figure 9:
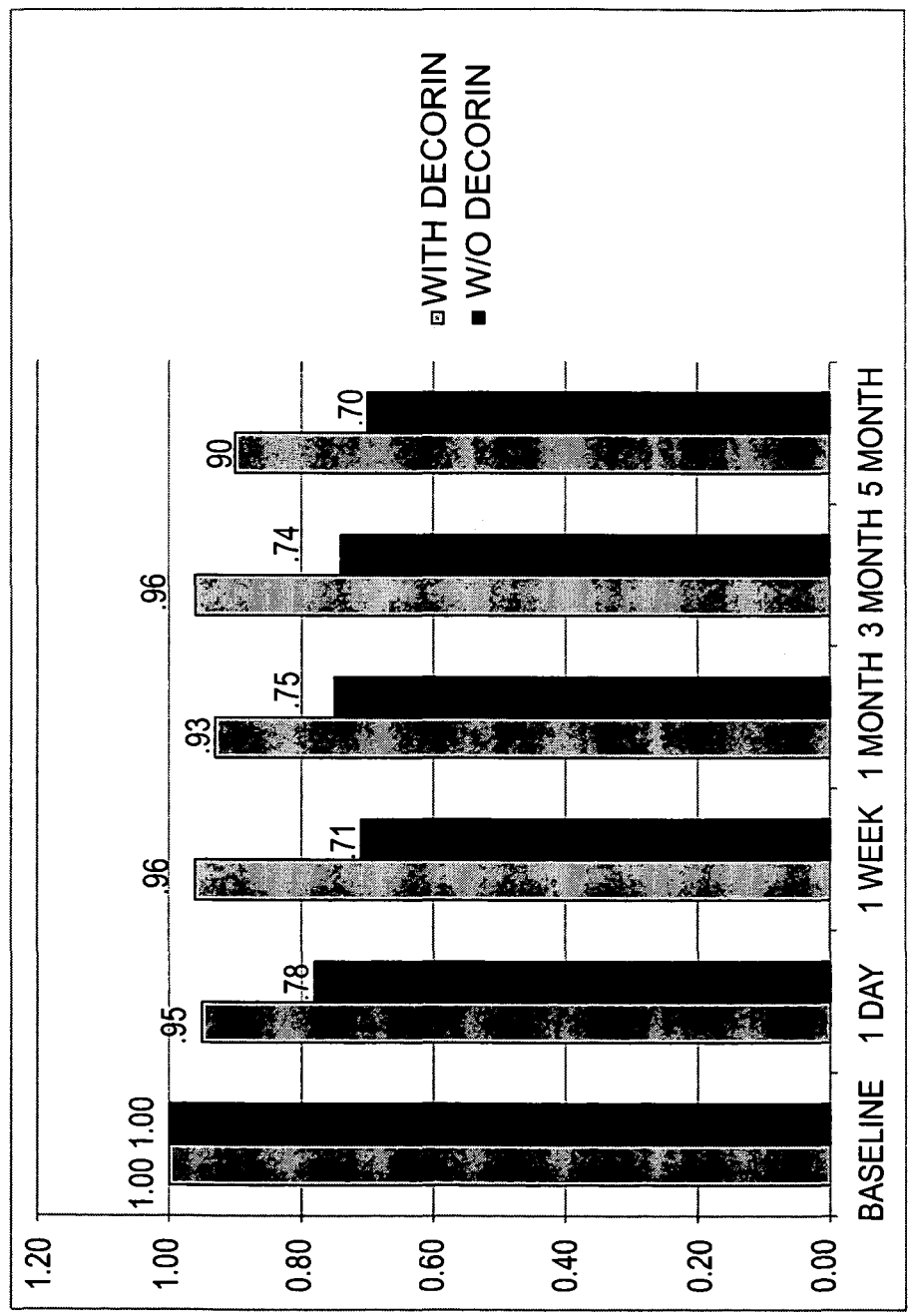
FIG. 9 shows the effects of decorin drops on corneal historesis for an individual patient.
Figure 10:
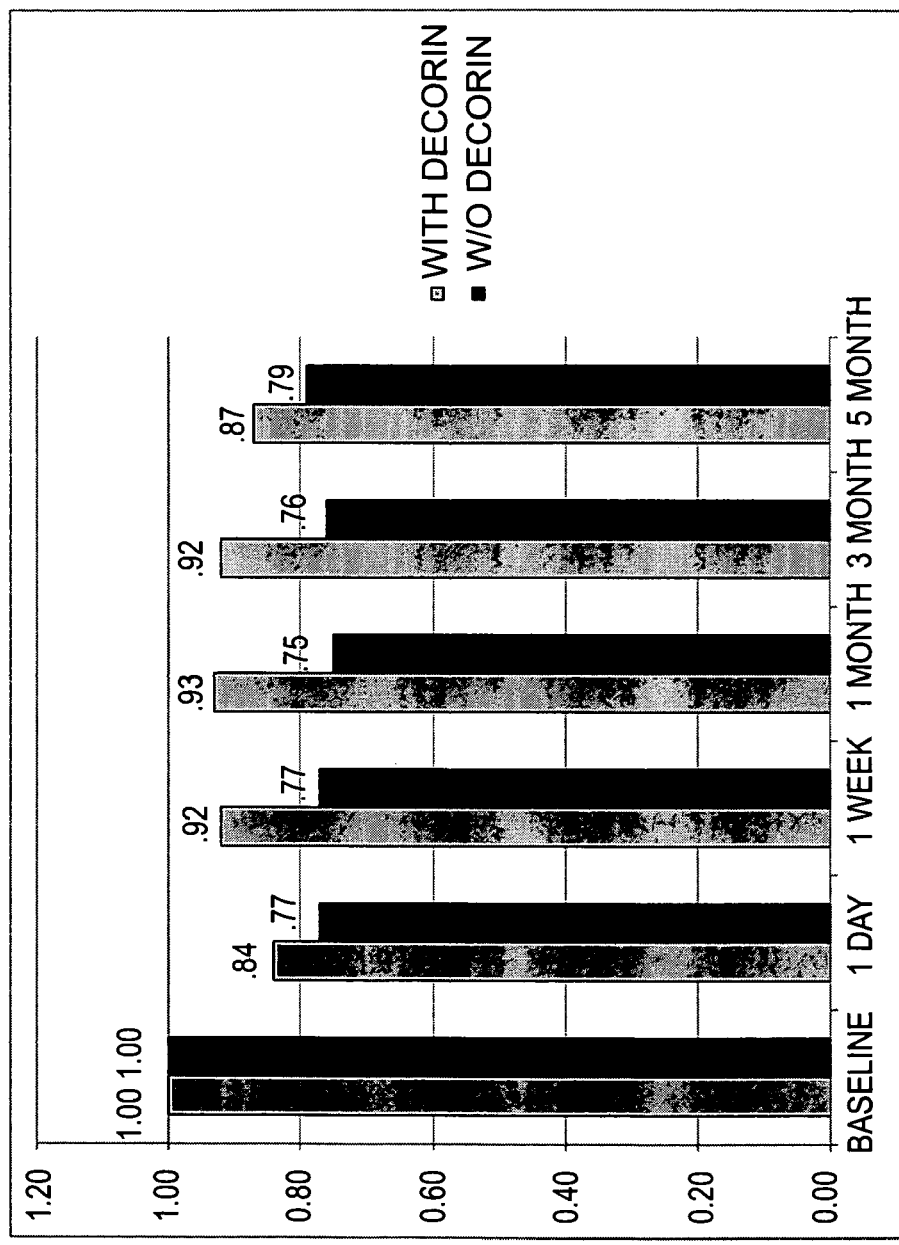
FIG. 10 shows the effects of decorin drops on corneal historesis for multiple patients.

The effects of decorin application on the biomechanical properties of the post-LASIK cornea were measured in five human myopic LASIK patients in a pilot study performed by Gabriel Carpio, MD at the Hospital Angeles, Mexico. Two drops of decorin solution were applied to the stromal bed during the LASIK procedure and one drop to the back of the surgical flap. In each patient, both eyes were subjected to LASIK, but only one eye received the decorin treatment (the treated eye). The other eye did not receive the decorin treatment and served as a control (the untreated eye). The biomechanical integrity of the cornea was measured using the Reichert Ocular Response Analyzer (ORA). FIGS. 9 and 10 show the difference in corneal hysteresis (CH) between the treated eyes and the untreated eyes from the time of treatment through a five-month follow-up period. FIG. 9 shows the effects of decorin drops on corneal historesis for an individual patient. FIG. 9 presents the data for an individual patient who had an OD of −6.25 and an OS of −6.00. The x-axis shows the time periods at which measurements were taken, i.e., at baseline and at various time points post surgery. The Y-axis shows the results as a percentage of baseline corneal historesis.

In the patient whose results are shown in FIG. 9, the corneal hysteresis of the treated eye exceeded that of the untreated eye at each time point post-LASIK procedure.

FIG. 10 shows the effects of decorin drops on corneal historesis for multiple patients. FIG. 10 groups the data for all five myopic patients in the study.

The grouped data in FIG. 10 shows improvement, at all time points, in corneal hysteresis in the treated eyes as compared to the untreated eyes. While these improvements are significant, even better results could be realized with an alternative delivery method.

Figure 11:
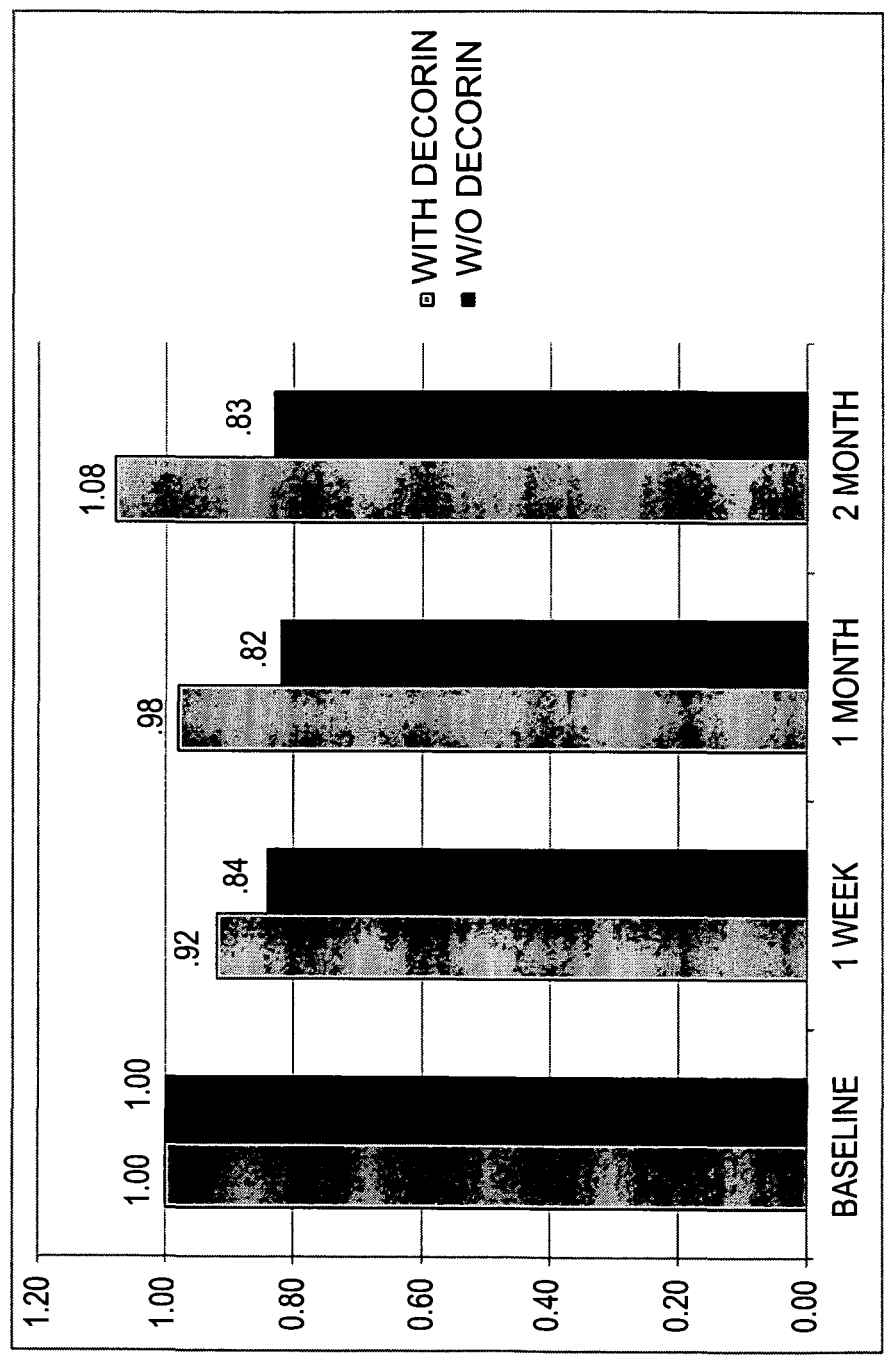
FIG. 11 shows the effects of decorin injections on corneal historesis for multiple patients.

In a preliminary clinical study, the decorin ophthalmic solution was administered, via injection, to LASIK patients during the surgical procedure. The contralateral treated eye served as the control. FIG. 11 shows the effects of decorin injections on corneal historesis for multiple patients. Results in FIG. 11 below show an increase in corneal hysteresis in LASIK eyes receiving injections of decorin into the stroma (rather than merely drops deposited on the surface of the stroma and on the underside of the flap).

For the patients shown in FIG. 11, decorin injections provided substantial strengthening of corneal structure following LASIK surgery and may reduce regression and the incidence of ectasia. It is also noteworthy that, on average, the corneal historesis is actually higher in the treated eyes two months after surgery than it was pre-surgery (i.e., at "baseline"). While there was hope that improvements in corneal historesis would be realized with decorin injection, as compared to those observed in patients receiving decorin drops, it was unexpected that corneal historesis would improve to a level that exceeded baseline.

Since the integrity/rigidity of the cornea can apparently be improved to a point higher than that naturally occurring in the patient, there are possibilities for using decorin injections beyond restoration of degraded corneal strength. For example, distortion of vision may occur with significant physical loads on the body, such as during sports and other activities that place high physical demands on the body, but still require a high level of visual acuity, e.g., playing high impact sports, flying fighter jets, or driving a race car.

A football player, such as a receiver, or a baseball player, such as an outfielder, must be able to see the ball even as his head bounces while running after the ball. It may be possible to improve a player's vision under these circumstances by injecting decorin to improve corneal rigidity, which may result in less temporary distortion of the corneal shape under loads experienced while running, jumping, and landing. Similarly, fighter pilots and race car drivers are subjected to high gravitational forces (G-forces, or simply "G's"), as well as bouncing/shaking forces due to turbulence or rough road surfaces. Such forces can result in temporary distortion of the corneal shape and, therefore, degraded vision. Thus, improvement of corneal rigidity with decorin injections may increase visual acuity under high activity-related loading.

In addition, in some embodiments, the disclosed injector device may be used to inject other types of agents, such as antibiotics, anti-inflammatory agents, anti-allergy agents, antihistamines, or any other ophthalmic solution that is desired to be delivered to subsurface regions of the stroma.

Although embodiments herein are shown and discussed as being configured for applications involving injection of solutions to the eye, embodiments are envisioned that may be configured for injection anywhere in or on the body. For example, features of the disclosed apparatus, such as needle insertion depth regulating means, various handle configurations and features, plunger actuating configurations, etc., may be adaptable for injectors used elsewhere in the body besides the eye. Similarly, various support structure or locator member configurations may be implemented according to the target area of injection. Exemplary non-ophthalmic uses may include, but are not limited to, insulin injections, antibiotic injections, anti-inflammatory injections for skin inflammation, anti-allergy injections, injection of anti-viral agents, etc. Additional possible uses may include surgical and non-surgical skin alterations (e.g., plastic/cosmetic surgery), for example, collagen, epithelial injections, Botox, etc. The volume of the hollow cavity, size of the needle, depth of injection, and other various parameters of the disclosed injector device may be selected appropriately for the area of the body being treated, and the type of agent injected.

Also, the disclosed devices may be utilized to aspirate liquids from the eye or other parts of the body. Possible uses may include specimen collection for various uses. For example, the disclosed devices may be utilized to take tissue samples, blood samples for various testing, (e.g., glucose testing), and other fluid samples, etc. Needle sizes may be determined according to the desired application. For example, embodiments configured for collecting tissue samples may have a needle with a larger inner diameter than embodiments utilized solely for fluid collection.

It must be noted that, as used herein and in the appended claims, the singular forms "a", "an" and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Unless defined otherwise, all technical and scientific terms used herein have the same meaning as commonly understood by one of ordinary skill in the art to which this invention belongs. All publications mentioned herein, including patents, patent applications, and publications are incorporated herein by reference in their entireties to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

While the presently disclosed device and method have been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step, or steps to the objective, spirit, and scope of the present invention. Other embodiments of the invention will be apparent to those skilled in the art from consideration of the specification and practice of the invention disclosed herein. It is intended that the specification and examples be considered as exemplary only.

What is claimed is:

1. An injector device configured to deliver an ophthalmic solution to a cornea of an eye, the injector device comprising:
a base including a locator member extending from a bottom portion of the base, wherein the locator member is configured to support the base over the cornea and is configured to contact a portion of the eye;
a needle connected to the base, configured to be inserted into the cornea to deliver the ophthalmic solution to the cornea, and disposed in a needle-holding member; wherein the needle-holding member is connected to the base at a point and configured to pivot about the point to insert the needle into the cornea.

2. The injector device of claim 1, further comprising a hollow cavity formed within the base and configured to contain the ophthalmic solution, wherein the needle is in fluid communication with the hollow cavity to deliver the ophthalmic solution to the cornea.

3. The injector device of claim 1, further comprising a penetration limiting element disposed on the needle, the penetration limiting element configured to regulate the depth of insertion of the needle within the cornea.

4. The injector device of claim 1, wherein the base comprises a plurality of locator members extending from a bottom portion of the base, wherein each locator member is configured to support the base over the cornea and each locator member is configured to contact a portion of the eye.

5. The injector device of claim 4, wherein the plurality comprises at least three locator members.

6. A method of delivering an ophthalmic solution to a cornea of an eye, the method comprising:
positioning a base of an injector device in contact with a portion of the eye;
aligning a needle that is connected to the base with the cornea, the needle being disposed within a needle-holding member;
inserting into the cornea the needle by pivoting the needle-holding member about a pivot point on the base; and
delivering the ophthalmic solution through an interior of the needle into the cornea.

7. The method of claim 6, wherein the ophthalmic solution comprises an antibiotic or anti-inflammatory agent to the cornea.

8. The method of claim 6, wherein the ophthalmic solution comprises decorin.

9. The method of claim 6, wherein the ophthalmic solution comprises transglutaminase.

10. The method of claim 6, wherein delivering further comprises delivering the ophthalmic solution from a reservoir connected to the needle via tubing, wherein the ophthalmic solution flows from the reservoir through the tubing and into the needle.

11. The method of claim 6, further comprising a penetration limiting element disposed on the needle with a surface of the cornea, the penetration limiting element configured to regulate the depth of insertion of the needle into the stroma of the eye.

12. The method of claim 6, wherein positioning further comprises holding a handle connected to the base so that a plurality of locator members disposed on a bottom of the base contacts the eye.

13. A method of placing an injector device on the eye, comprising:
a) contacting the eye with an injector device configured to deliver an ophthalmic solution to a cornea of an eye, the injector device comprising:
a base including a locator member extending from a bottom portion of the base, wherein the locator member is configured to support the base over the cornea and is configured to contact a portion of the eye;
a needle connected to the base, configured to be inserted into the cornea to deliver the ophthalmic solution to the cornea, and disposed in a needle-holding member; wherein the needle-holding member is connected to the base at a point and configured to pivot about the point to insert the needle into the cornea;
thereby placing an injector device on the eye.

14. The method of claim 13, further comprising:
b) inserting into the cornea the needle by pivoting the needle-holding member about a pivot point on the base.

15. The method of claim 13, further comprising:
c) delivering the ophthalmic solution through an interior of the needle into the cornea.

16. The injector device of claim 13, wherein the base comprises a plurality of locator members extending from a bottom portion of the base, wherein each locator member is configured to support the base over the cornea and each locator member is configured to contact a portion of the eye.

17. The injector device of claim 16, wherein the plurality comprises at least three locator members.

* * * * *